United States Patent [19]

Sklavounos

[11] Patent Number: 4,709,044
[45] Date of Patent: Nov. 24, 1987

[54] BIOTIN INTERMEDIATES

[75] Inventor: Constantine Sklavounos, Waterford, Conn.

[73] Assignee: Pfizer Inc., New York, N.Y.

[21] Appl. No.: 879,231

[22] PCT Filed: Sep. 26, 1984

[86] PCT No.: PCT/US84/01563

§ 371 Date: May 23, 1986

§ 102(e) Date: May 23, 1986

[87] PCT Pub. No.: WO86/02069

PCT Pub. Date: Apr. 10, 1986

[51] Int. Cl.$^4$ ............................................. C07D 233/38
[52] U.S. Cl. ..................................... 548/321; 548/303
[58] Field of Search ............................................ 548/321

[56] References Cited

U.S. PATENT DOCUMENTS 3,960,884  6/1976  Zavyalov et al. .................... 548/303

FOREIGN PATENT DOCUMENTS 1419927  12/1975  United Kingdom ................ 548/303

OTHER PUBLICATIONS

March, J., *Advanced Organic Chemistry*, McGraw Hill, New York, 1968, p. 330.
C.A. 94: 15640y; Zavyalov et al., *Izv. Akad. Nauk SSSR*, Ser. Khim, 1980, pp. 1943–1945 (including original article and translation).
C.A. 84: 31061; Mukaiyama et al., Japan Kokai No. 75 88,086 (1975) (Abstract only).
C.A. 79: 105143h; Zavyalov et al., *Izv. Akad. Nauk SSSR*, Ser. Khim, 1973, pp. 1679–1681 (Abstract only).
T. Taquchi et al., *Chemistry Letters* 1974, pp. 729–730.

Primary Examiner—Richard A. Schwartz
Attorney, Agent, or Firm—Peter C. Richardson; Albert E. Frost; Robert K. Blackwood

[57] ABSTRACT

In the synthesis of biotin and decarboxybiotin, a more direct method for the conversion of 1,3-diacyl-4-(bromomethyl)-5-[(5-alkoxycarbonylpentanoyl) or hexanoyl]-4-imidazolin-2-ones to 1,3-diacyl-4-[(4-alkoxybutanoyl) or pentanoyl]-1H,3H-thieno(3,4-b)imidazol-2-one via the Bunte salt of the formula

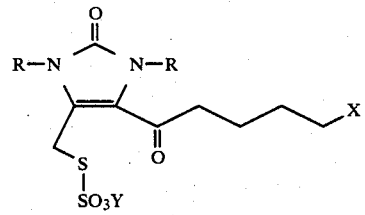

wherein R is $(C_1-C_5)$alkanoyl or $(C_2-C_5)$alkoxycarbonyl, X is methyl or $(C_2-C_5)$alkoxycarbonyl and Y is an alkali metal.

5 Claims, No Drawings 4,709,044

BIOTIN INTERMEDIATES

BACKGROUND OF THE INVENTION

In the synthesis of biotin or of so-called decarboxybiotin (in which the carboxy group of biotin has been replaced by a methyl group), the present invention provides an improved, more direct method for the conversion of a 1,3-diacyl-4-(bromomethyl)-5-[(5-alkoxycarbonylpentanoyl) or hexanoyl]-4-imidazolin-2-one, of the formula

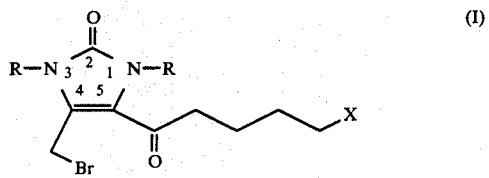

wherein R is $(C_1-C_5)$alkanoyl or $(C_2-C_5)$alkoxycarbonyl and X is methyl or $(C_2-C_5)$alkoxycarbonyl, to a 1,3-diacyl-4-[(4-alkoxybutanoyl) or pentanoyl]-1H,3Hthieno(3,4-b)imidazoyl-2-one of the formula

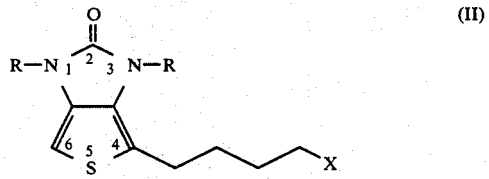

wherein R and X are as defined above. The present method proceeds via the Bunte salt of the formula

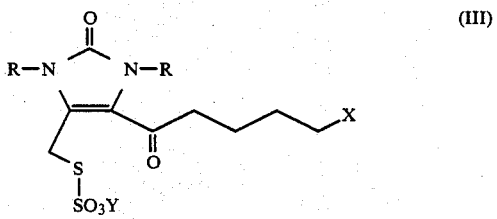

wherein R and X are as defined above and Y represents an alkali metal (lithium, sodium or potassium).

Heretofor Mukaiyama et al., Japanese Kokai No. 75-88,086 (Chemical Abstracts 84:31061) transformed compound (I) wherein R is acetyl and X is ethoxycarbonyl by reaction of (I) with thiolacetic acid, forming the 4-(acetylthiomethyl) derivative, followed by cyclization to the thienoimidazolone in acetic acid in the presence of dry HCl—with concurrent hydrolysis of the ethyl ester and loss of the acetyl groups. The latter groups must be replaced in an added step because of their importance in facilitating the next stage (hydrogenation) of biotin synthesis. In like manner, Za'ylov et al. [A], Izv. Akad. Nauk. SSSR, Ser. Khim. 1973, pp. 1679-1681 (Chem. Abstracts 79:105143h) have cyclized the same 4-(acetylthiomethyl) derivative with aqueous NaOH followed by aqueous HCl, again with concurrent hydrolysis and loss of both acetyl groups; see also Russian patent 579,767 where cyclization is accomplished with p-toluenesulfonic acid in methanol, again with loss of both acetyl groups (now with conversion to methyl ester rather than hydrolysis to the carboxylic acid).

Similarly, Zav'yalov et al. [B], Isv. Akad. Nauk. SSSR, Ser. Khim. 1980, pp. 1943-1945 .Chem. Abstracts 94:15640y) transformed the compound (I) wherein R is acetyl and X is methoxycarbonyl by reaction of (I) with N-benzoylthiourea to form the isothiuronium salt [43CH$_2$SC(=NH)NHCOC$_6$H$_5$.HBr], followed by cyclization in methanol-p-toluene sulfonic acid, again with loss of both acetyl groups. The highly noxious odor problems associated with this, as well as the above processes employing acetylthio intermediates, represents another major disadvantage of these processes—a disadvantage which is not shared by the present process.

Although Zav'yalov et al. [B] reacted 4(chloromethyl)-5-(5-ethoxycarbonylpentanoyl)-4-imidazolin-2-one with sodium thiosulfate in ethanol at room temperature, followed by addition of p-toluenesulfonic acid and boiling, to form a poor yield 4-(4-ethoxycarbonylbutanoyl)-1H,3H-thieno[3,4-d]imidazol-2-one requiring chromatographic purification, they report that attempted, analogous cyclization of the acetylated compound of the above formula (III), wherein R is acetyl, X is ethoxycarbonyl and Y is sodium was not successful at all, there being formed instead the deacetylated methyl ether:

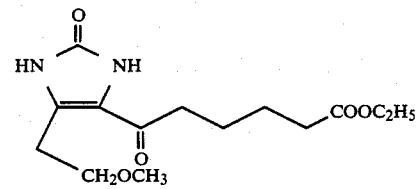

Zav'yalov et al. offer no specific experimental method for preparation, isolation or characterization of the diacetylated thiosulfate salt derivative which they attempted to cyclize.

SUMMARY OF THE INVENTION

In spite of the above results of Murkaiyama et al. and Zav'yalov et al., we have found mild conditions under which the Bunte salts of the formula (III) are not only readily cyclized to the desired biotin precursors of the above formula (II), but the cyclization occurs in high yield, without loss of N-acyl groups, and without need for chromatography in the isolation of purified products. The cyclization reaction is carried out in a reaction-inert solvent in the presence of at least a catalytic amount of both water and a strong acid catalyst. Although the levels of water and acid catalyst are not critical, it is convenient and advantageous to use about one molar equivalent each of water and strong acid so as to effect clean and complete reaction within a reasonable period of time. Temperature is likewise not critical, but is preferably in the range of 0°-50° C., conveniently at ambient temperature (e.g., 17°-27° C.) avoiding the energy wasting heating or cooling of the reaction mixture.

As used herein, the expression reaction-inert solvent is intended to specify a solvent which does not interact with reagents, intermediates or products in a manner which will adversely affect the yield of the desired product. In the present instance, the preferred solvent is a $(C_1-C_5)$alkanoic acid, particularly acetic acid. Although a catalytic amount of water (e.g. up to a few molar equivalents) is desired in the reaction, larger quantities are to be avoided, particularly when the temperature is higher in or above the preferred range. High levels of lower alkanols, particularly primary alcohols or methanol are also to be avoided in the solvent.

Suitable strong acids include, but are not limited to, benzenesulfonic acid, p-toluenesulfonic acid, (anhydrous or monohydrate), methanesulfonic acid, hydrogen chloride, hydrogen bromide, sulfuric acid, nitric acid and phosphoric acid. The preferred values of R are acetyl, propionyl or methoxycarbonyl. The preferred values of X are methyl, methoxycarbonyl and ethoxycarbonyl.

DETAILED DESCRIPTION OF THE INVENTION

The present invention is readily carried out, in spite of the contrary expectation based on the prior art, particularly above cited Zav'yalov et al. [B].

Bromomethyl compounds of the above formula (I), are first converted to the Bunte salts (III), conveniently by reaction of substantially equimolar quantities of (I) and an alkali metal thiosulfate in a reaction-inert solvent at 0°–50° C. Well-suited conditions are sodium thiosulfate pentahydrate in aqueous acetonitrile or tetrahydrofuran at ambient temperature. At some time after the reaction is substantially complete (generally not before 0.5 to 1.5 hours under the suggested specific conditions) the reaction is evaporated to dryness, with azeotropic removal of traces of water by reevaporation with a solvent such as toluene, if desired, to yield the desired Bunte salt, together with an equimolar amount of alkali metal bromide. This resulting mixture is perfectly well-suited for cyclization, there being no need to remove the by-product bromide salt.

The cyclization is carried out according to the methods in the summary section above, as specifically exemplified below.

The required bromomethyl precursors are prepared by known methods. Particularly well suited methods are described in the specific examples below, which include the advantageous method of Andrews for the preparation of 4-methyl-4-imidazolin-2-one. The latter is the subject of concurrently filed P.C.T. patent application, Ser. No. PCT/US84/01562 (U.S. Ser. No. 897,004).

The products (II) of the present invention are converted to biotin according to known chemical or biological methods. For example, see Izumi et al., in Advances in Applied Microbiology, D. Perlman ed., Vol. 22, pp. 145–176 (1977); Ogino et al., U.S. Pat. No. 3,859,167 (1975); Vasilevskis, U.S. Pat. No. 4,130,712 (1978).

The present invention is illustrated by the following examples. However, it should be understood that the invention is not limited to the specific details of these examples.

EXAMPLE 1

4-Methyl-4-imidazolin-2one

A solution of 166.3 g (2.77 mol) of urea, 215.2 g (2.90 mol) of acetol in 850 ml of acetic acid containing 50 mg of phosphomolybdic acid catalyst was heated for 2.5 hours at 125° C. On cooling, the reaction was evaporated under vacuum to a dark brown oil (43% yield by hplc analysis on a Waters Ass. micro-bondapack $C_{18}$ column using acetonitrile/water 1:9 as eluant at a flow rate of 0.3 ml min and refractive index detection). The oil was dissolved in 300 ml of dioxane and reevaporated to azeotropically remove residual acetic acid, then dissolved in 800 ml of water, the pH adjusted to 7.0–8.5 with solid calcium hydroxide, treated with diatomaceous earth and filtered. The filtrate was washed twice with 250 ml of isopropylether, and concentrated in vacuo to a volume of 712 ml. The resulting solution was chromatographed by ion exclusion in three batches on a 10 cm×76 cm column packed with 3.4 kg of Dowex 50W-x2 (sulfonated styrenedivinylbenzene copolymer with 2% cross-linking) 50–100 mesh resin (Ca++ form) Elution was with water at 55° C. taking 500 ml fractions. Fractions 10–13 of each run were combined and evaporated in vacuo to afford 127.4 g of a light yellow solid shown to be 53% pure imidazolinone (26% yield). This material is sufficiently pure to be used in the subsequent acylation step of Examples 5–9. Recrystallization from 375 ml of water afforded 45 g (17%) of pure imidazolinone: m.p. 204–208° C.; $^1$H-NMR (DMSO-$d_6$): 1.91 (s, 3, $CH_3$), 5.93 (s, 1, C=CH); $^{13}$C-NMR (DMSO-$d_6$): 155.2 (s, $(N)_2C$=O), 117.4 (s, =C—$CH_3$), 104.1 (d, =CH), 10.5 (q, $CH_3$): IR (KBR) cm$^{-1}$: 3210 (s, N—H), 1680 (s, C=O).

Analysis Calculated for $C_4H_6N_2O$: C, 48 97; H, 6.15; N, 28.56%. Found: C, 48.73; H, 6.31; N, 28.66%.

EXAMPLE 2

4-Methyl-4-imidazolin-2-one

A solution of 97.3 g (1.62 mol) of urea and 100 g (1.35 mol) of acetol in 500 ml of acetic acid was heated 4 hours at 130° C., whereupon the acetic acid was removed by distillation at reduced pressure, affording a brown, viscous oil containing the imidazolinone in 43% yield by hplc analysis. To the oil was added 350 ml of dioxane and the solvent was again removed by distillation to a second oil which was dissolved in 400 ml of water, extracted two times with 100 ml of isopropyl ether and adjusted with 6N sodium hydroxide to pH 7. The water was removed by distillation to leave a heavy oil (259 g). The latter was placed on a short column containing 500 g of silica gel. Elution with 90/10 ethyl acetate/methanol afforded, on evaporation of the fraction, 118 g of crude imidazolinone. The crude material was dissolved in 250 ml of water and allowed to crystallize in the cold overnight. The crystals were isolated by filtration and air dried to afford 25 g (first crop) and 14.4 g (second crop) for a total yield of 39.4 g (0.42 mol) of hplc homogenous product.

EXAMPLE 3

4-Methyl-4-imidazolin-2-one

To 600 ml of acetic acid was added 150 g (2 mol) of acetol followed by 62 g (1 mol) of urea. The reaction mixture was heated to reflux in a flask fitted with a Dean-stark trap. Approximately 60 ml of liquid was removed over 2 hours. The reaction was continued an additional 30 minutes whereupon (tlc) analysis showed the absence of urea. The acetic acid was removed under vacuum and the residue dissolved in 500 ml of water. The solution was treated with 600 g of AG1-x8 resin (Rohm and Haas Inc.), filtered and concentrated to 200 ml. The solution was cooled in a refrigerator overnight to afford a mass of yellow crystals which were collected and air dried (20.6 g). Concentration of the mother liquor and cooling afforded a second crop (7.0 g). The total yield was 27.6 g (0.28 mol, 28%).

EXAMPLE 4

Table 1 sets forth alternative reaction conditions and yields of 4-methyl-4-imidazolin-2-one in the reaction between acetol and urea in acetic acid. In all cases, the concentration of urea in acetic acid was 20%.

TABLE 1

| Urea (g) | (moles) | Acetol (g) | (moles) | Temperature (°C.) | Time (hours) | Yield by Assay (%) |
|---|---|---|---|---|---|---|
| 1.2 | (0.02) | 1.78 | (0.024) | reflux | 5 | 39 (a) |
| 1.2 | (0.02) | 1.48 | (0.02) | 60 | 4 | 2 |
| 1.2 | (0.02) | 1.48 | (0.02) | 60 | 4 | 2 (b) |
| 1.2 | (0.02) | 1.48 | (0.02) | 100 | 4 | 36 |
| 1.2 | (0.02) | 2.96 | (0.04) | 120 | 4 | 50 |
| 10.0 | (0.166) | 24.66 | (0.342) | 100 | 5.5 | 39 |
| 10.0 | (0.166) | 24.66 | (0.342) | 120 | 4 | 32 |
| 10.0 | (0.166) | 24.66 | (0.342) | 100 | 16 | 39 (nmr) |
| 10.0 | (0.166) | 14.7 | (0.20) | 130 | 16 | 43 (nmr) |
| 10.0 | (0.166) | 14.7 | (0.20) | 100 | 16 | 40 (nmr) (b) |
| 10.0 | (0.166) | 14.7 | (0.20) | 100 | 16 | 38 (nmr) (c) |
| 6.14 | (0.083) | 10.0 | (0.166) | 100 | 16 | 50 (nmr) |
| 63.0 | (0.83) | 100 | (1.66) | 100 | 2 | — |
| 25 | (0.41) | 36.9 | (0.82) | 100 | 16 | — |
| 10 | (0.166) | 14.7 | (0.199) | 100 | 16 | 24 (nmr) (d) |
| 10 | (0.166) | 14.7 | (0.199) | 100 | 16 | 16 (nmr) (e) |
| 97.3 | (1.62) | 100 | (1.35) | 130 | 4 | — |
| 97.3 | (1.62) | 100 | (1.35) | 130 | 4 | (30)* |
| 97.3 | (1.62) | 100 | (1.35) | 130 | 5 | (15)* |
| 97.3 | (1.62) | 100 | (1.35) | 130 | 5 | 42 |
| 97.3 | (1.62) | 100 | (1.35) | 130 | 7 | 35 |
| 97.3 | (1.62) | 100 | (1.35) | 130 | 1 | 43 |
| 97.3 | (1.62) | 100 | (1.35) | 130 | 1 | 44 |
| 10.0 | (0.166) | 12.3 | (0.166) | 100 | 4 | 43 |
| 10.0 | (0.166) | 12.3 | (0.166) | 100 | 3 | 0 (nmr) (f) |
| 5.0 | (0.083) | 6.1 | (0.083) | 130 | 1 | 0.1 (nmr) (g) |
| 10.0 | (0.166) | 12.3 | (0.166) | 120 | 2 | 43 (nmr) |
| 10.0 | (0.166) | 12.3 | (0.166) | 120 | 1 | 30 (nmr) (h) |
| 10.0 | (0.166) | 12.3 | (0.166) | 120 | .5 | 35 (nmr) (i) |
| 10.0 | (0.166) | 12.3 | (0.166) | 120 | .5 | 35 (nmr) (j) |
| 10.0 | (0.166) | 12.3 | (0.166) | 120 | .5 | 35 (nmr) (k) |
| 10.0 | (0.166) | 12.3 | (0.166) | 120 | 2 | 48 (nmr) (l) |
| 166 | (2.77) | 215 | (2.8) | 125 | 2 | 43 (l) |
| 166 | (2.77) | 215 | (2.6) | 120 | 2 | 44 |
| 62.0 | (1.03) | 150 | (2.03) | reflux | 1 | (27)* (m) |

(a) Azeotropic removal of water.
(b) Tetra-n-butylammonium hydrogen sulfate (1%) added as catalyst.
(c) $ZnBr_2$ added as catalyst.
(d) One equivalent of acetic anhydride (0.166 mol) added as water scavenger.
(e) $ZnCl_2$ added as catalyst, acetic anhydride (0.166 mol) added.
(f) Formic acid used as solvent instead of acetic acid.
(g) Reaction performed neat without the addition of solvent.
(h) One equivalent of acetic anhydride added dropwise over 1 hour.
(i) Used 1N sodium acetate in acetic acid as solvent.
(j) Used 1N calcium acetate in acetic acid as solvent.
(k) Used 1M pyridine in acetic acid as solvent.
(l) Used 10 mg phosphomolybdic acid as catalyst.
(m) Used AG1 × 8 resin to remove acetic acid, then direct crystallization.
*Isolated yield. Yield is otherwise by hplc assay unless (nmr) is indicated.

EXAMPLE 5

4-Methyl-5-(5-ethoxycarbonylpentanoyl)-4-imidazolin-2-one

To a 2 1 3-necked round-bottom flask equipped with mechanical stirrer, reflux condenser and nitrogen inlet was added 30 g (0.306 mol) of 4-methyl-4-imidazolin-2-one, 250 ml of $CHCl_3$ and 147 g (1.22 mol) of dry sulfolane. To the rapidly stirring solution at ice-bath temperature was added 163 g (1.22 mol) of $AlCl_3$ portionwise. The ice bath was removed and the reaction mixture heated to 75° C. whereupon 64.6 g (0.312 mol) of 5-ethoxycarbonylpentanoyl chloride was added dropwise over 1 hour. After stirring an additional 2 hours the reaction mixture was poured into 1.5 g of rapidly stirred ice containing 45 g of sodium carbonate. A yellow oil separated from solution. The resulting mixture was treated with 800 ml of ethyl ether and stirred an additional 15 minutes to afford a white solid which was isolated by filtration. The solids were washed with ether and dried overnight under vacuum to afford 76 g (98% crude yield) of the desired ketoester shown by hplc analysis (Waters Ass. Microbondapac $C_{18}$ column using acetonitrile/water 2:3 as eluant and 0.3 ml/min flow rate) to be 87% pure (an 84% yield of ketoester corrected for purity) The crude solids were recrystallized from 1:1 ethanol/water to afford 53.1 g (68%, first crop) of ketoester m.p. 171–174° C.; IR (KBr) cm$^{-1}$: 3452 (s), 3169 (s), 1738 (s), 1696 (s), 1641 (s), 1608 (m); $^1$H-NMR (DMSO-D$_6$): 4.03 (q, 2), 2.50 (m, 4), 2.28 (s, 3), 1.59 (m, 4), 1.19 (t, 3): $^{13}$C-NMR (DMSO-d$_6$): 188.6 (s), 172.9 (s), 152.7 (s), 129.8 (s), 119.1 (s), 59.7 (q), 38.5 (t), 33.4 (t), 24.1 (t), 23.1 (t), 14 1 (q), 11.7 (q): mass spectrum (70 eV) m/e 254 (parent), 209 (p-OEt), 125 (base).

Analysis Calculated for $C_{12}H_{18}N_2O_4$; C, 56.67; H, 7.13; N, 11.01%. Found: C, 56.72; H, 7.05; N, 10 85%

EXAMPLE 6

4-Methyl-5-(5-ethoxycarbonylpentanoyl)-4-imidazolin-2-one

A mixture of 166.3 g (2.77 mol) of urea, 215.2 g (2.90 mol) of acetol and 850 ml of acetic acid was heated under a nitrogen atmosphere at 125° C. for 2.5 hours whereupon the acetic acid solvent was removed by rotary evaporation to a mobile brown oil. The oil was taken up in 300 ml of dioxane and reevaporated in vacuum. The cycle was repeated one time and the resulting brown oil (409.7 g, 44% yield of intermediate 4-methyl-4-imidazolin-2-one by hplc analysis) was dissolved in water to a volume of 900 ml. The aqueous solution was adjusted to pH 8.5 with solid calcium hydroxide, treated with 10 g diatomaceous earth and filtered. To the filtrate was added 1.5 l of acetone, the precipitated calcium acetate was removed by filtration (198 g) and the filtrate evaporated to 310 g of oil. The oil was triturated with three volumes of ethyl acetate and the residue evaporated to 129 g of crude 4-methyl-4-imidazolin-2-one as a yellow solid (purity by hplc 36%, representing a 29% corrected yield of this intermediate).

A slurry of this crude intermediate [containing 10.6 g (.0.108 mol) of 4-methyl-4iimidazolin-2-one by assay] in 51.8 g of sulfolane and 100 ml of chloroform was cooled to ice bath temperature in a 3-necked round bottom flask equipped with reflux condenser, nitrogen inlet, nitrogen outlet, mechanical stirrer and addition funnel and 71.8 g (0.540 mol) of AlCl$_3$ added portionwise. After the addition was complete, the temperature of the bath was raised to 75° C. and 29.0 g (0.151 mol) of ethyl 5-ethoxycarbonylpentanoyl chloride added dropwise over a 60 minute period. On heating an additional 1.5 hours, tlc (silica gel, methanol/ethyl acetate 1:4, UV followed by phosphomolybdic acid visualization) suggested the complete consumption of starting material and the formation of the desired ketoester. The reaction mixture was then poured onto 500 ml of ice containing 16 g of sodium carbonate dissolved in 50 ml of water. The aqueous hydrolysis mixture was stirred rapidly while 400 ml of ethyl ether was added. After 15 minutes the precipitated solid was removed by filtration, washed with ether and dried overnight under vacuum to afford 30.0 g of tan solid shown to be 76% pure by hplc analysis (83% yield corrected for purity). The solid was recrystallized from 1:1 ethanol:water to yield 16.7 g of purified title product, homogeneous by hplc and tlc, m.p. 170°-172° C., identical in physical properties to the product of the preceding Example.

EXAMPLE 7

4-Methyl-4-imidazolin-2-one

To a solution of 48.0 g of urea in 70 ml of acetic acid at 80° C. was added 20.8 g of acetol and 10 mg of phosphomolybdic acid. The resulting reaction mixture was refluxed for 1.5 hour, then evaporated in vacuo to 94.5 g and the residue taken up in 95 ml of water, the pH adjusted to 7.8 with solid sodium carbonate and the aqueous solution extracted with 3×190 ml of n-butanol. The combined butanol extracts were washed 1×50 ml brine, evaporated to 350 ml, cooled and stored at 0° C. for 16 hours. A white solid separated out and was removed by filtration. The filtrate was evaporated to dryness and the residue taken up in about 10 ml of hot water. On cooling to 0°-5° C., title product crystallized and was collected by filtration. Recrystallization from 10 ml of water gave 5.5 g (20%) of the purified title compound, identical with the product of Example 1.

Alternatively, a mixture of 640 ml of glacial acetic acid and 538.1 g of urea was heated on an oil bath at 125° C. until a clear solution was obtained, whereupon 331.9 g of acetol was added. The mixture was stirred at 125° C. for 1 hour. On cooling to 60° C., 350 g of volatiles were removed in vacuo, and 220 g of sodium carbonate monohydrate added. The pH of the mixture was adjusted to 9.6 by the dropwise addition of 10N sodium hydroxide solution. The resulting mixture was extracted twice with 1 liter portions of methylene chloride and four times with 1.5 liter of n-pentanol. The combined n-pentanol layers were evaporated in vacuo, the residue taken up in about 125 ml of water, and the aqueous solution was cooled to 0°-5° C. The resulting crystalline crude product was collected by filtration and washed with 2×25 ml of ice-water. After drying, this material was recrystallized from 150 ml of water to give 77.3 g (12.6%) of the purified title compound, identical with the product of Example 1.

EXAMPLE 8

4-Methyl-5-(5-methoxycarbonylpentanoyl)-4-imidazolid-2-one

A 3-necked round-bottom flask equipped with mechanical stirrer, nitrogen inlet and addition funnel was charged with a suspension of 30 g (0.306 mol) of 4-methyl-4-imidazolid-2-one in 200 ml of nitrobenzene, cooled to 10° C., and 122 g (0.918 mol) of AlCl$_3$ was added portionwise with vigorous stirring. The resulting brown slurry was heated at 65° C. for 5 hours by which time HCl evolution had ceased. The viscous brown oil was poured slowly onto 1 liter of ice containing 113.8 g of Na$_2$CO$_3$. H$_2$O. A heavy, oily suspension formed, to which was added 1 liter of ethyl ether. After stirring for 30 minutes, the precipitated material was recovered by filtration affording 83 g of a gummy solid which was dried at 50° C. under vacuum overnight to yield 50 g of tan solid. The latter was recrystallized from 150 ml of ethanol/water to afford 20.5 g (29%) of crystalline title product; m.p. 172°-172.5° C.; IR (KBr) cm$^{-1}$: 3279 (s, N—H), 1724 (s, ester C=O), 1621 (s, C=C); $^1$H-NMR (DMSO-d$_6$): 10.18 and 10.84 (s, 2, N—H, D$_2$O exchangeable), 3.55 (s, 3, CH$_3$—O), 2.25 (s, 3, CH$_3$-C), 1.50 (m, 4, —CH—); $^{13}$C—NMR (DMSO-d$_6$): 188.3 (s, O=C), 173.2 (s, ester C=O), 152.6 (s, (N)$_2$C=O), 129.9 (s), 119.0 (s), 51.3 (q, CH$_3$—O), 38.7, 33.7, 24.3, 23.2, 11.9 (q, CH$_3$—).

Analysis Calculated for C$_{11}$H$_{16}$N$_2$O$_4$: C, 54.97; H, 6.71; N, 11.66%. Found: C, 54.71; H, 6.77; N, 11.36%.

EXAMPLE 9

4-Methyl-5-hexanoyl-4-imidazolin-2-one

A flask equipped with mechanical stirrer, reflux condenser and nitrogen inlet, was charged with 5.0 g (0.051 mol) of 4-methyl-4-imidazolin-2-one in 40 ml of nitrobenzene and cooled to ice-bath temperature. Aluminum chloride (27.1 g, 0.204 mol) was added portionwise. The reaction was heated to 75° C. and 7.55 g (0.056 mol) of hexanoyl chloride was added dropwise over 1 hour. Heating was continued for an additional 5 hours whereupon all starting material had been consumed as evidenced by tlc analysis (silica gel, methanol/ethyl acetate 1:4, phosphomolybdic acid visualization). The reaction was poured onto 100 ml of ice containing 7.5 g of sodium carbonate dissolved in 25 ml of water. The reaction mixture was stirred rapidly while 100 ml of ether were added. The resulting solids were isolated by filtration to afford after drying 5.2 g of crude ketone. The crude solids were recrystallized from 50 ml of water/ethanol 1:1 to afford 3.1 g (31%) of homogeneous title product; m.p. 221°-223° C.; IR (KBr) cm$^{-1}$:

3178 (s), 3153 (s), 3106 (s), 1746 (s), 1714 (s), 1657 (s), 1644 (s), 1611 (s); $^1$H-NMR (DMSO-d$_6$): 10.17 (s, 2, N—H), 2.5 (m), 2.27 (s, 3), 1.34 (m, 6), 0.86 (t, 3); $^{13}$C-NMR (DMSO-d$_6$): 188.5, 152.4, 118.9, 129.4, 38.8, 31.0, 23.4, 22.0, 13.8, 11.7; mass spectrum (70 eV) m/e 196 (parent), 140 C$_6$H$_8$O$_2$,base), 125 (C$_5$H$_5$N$_2$O$_2$).

Analysis Calculated for C$_{10}$H$_{16}$N$_2$O$_2$. C, 61.20; H, 8.21; N, 14.27%. Found: C, 61.12; H, 8.07; N, 14.45%.

EXAMPLE 10 dl-Desthiobiotin

A solution of 1.5 g (6.63 mmol) of 4-methyl-5-(5-carboxypentanoyl)-4-imidazolin-2-one in 30 ml of acetic acid was hydrogenated in a Parr shaker apparatus over 0.4 g of PtO$_2$ at 3 atmospheres and ambient temperature for 3 hours until hydrogen uptake ceased. The Pt was removed by filtration and the filtrate concentrated to an oil comprising 1.1 g. The oil was dissolved in water and cooled overnight to afford 0.9 g (64%) of dl-desthiobiotin identical in all respects to authentic material.

EXAMPLE 11

Ethyl Ester of dl-Desthiobiotin

A solution of 10.0 g (0.039 mol) of 4-methyl-5-(5-ethoxycarbonylpentanoyl)-4-imidazolin-2-one in 100 ml of acetic acid was hydrogenated on a Paar shaker apparatus over 5.0 g of PtO$_2$ (pre-reduced in 100 ml of acetic acid and isolated by filtration under nitrogen) at 4 atmospheres and 50° C. for 18 hours, affording the theoretical uptake of hydrogen (0.117 mol). The catalyst was removed by filtration, washed with acetic acid and the combined filtrate was roto-evaporated to dryness affording 10.1 g (91% by hplc analysis) of a semicrystalline solid shown to be homogeneous by hplc analysis (3 mm×20 cm column using a C-18 stationary phase and 60:40 H$_2$O:CH$_3$CN mobile phase at a flow rate of 1.0 ml/min). A sample was recrystallized from ethanol for analysis; m.p. 45°-52° C.; $^1$H-NMR (CDCl$_3$): 5.63 and 5.42 (s, 2, H—N, D$_2$O exchangeable), 4.1 (q, 2), 3.69 (m, 2), 2.27 (t, 2), 1.38 (m, 8), 1.11 (t, 3), 1.08 (d, 3); $^{13}$C-NMR (CDCl$_3$): 173.2 (s), 163.7 (s), 60.0 (t), 55.9 (d), 51.2 (d), 34.1 (t), 29.5 (t), 28.9 (t), 26.0 (t), 24.6 (t), 15.6 (q), 14.2 (q).

Analysis Calculated for C$_{12}$H$_{22}$N$_2$O$_3$: C, 59.37; H, 9.15; N, 11.56%. Found: C, 59.12; H, 8.94; N, 11.48%.

By the same method, 4-methyl-5-(5-methoxycarbonyl)-4-imidazolin-2-one is converted to the methyl ester of dl-desthiobiotin.

EXAMPLE 12 dl-Desthiobiotin

To a solution of 9.7 g of dl-desthiobiotin ethyl ester in 10 ml of ethanol heated to 50° C. was added 50 ml of 1N aqueous NaOH dropwise over a period of 20 minutes. After heating an additional 60 minutes, the reaction was cooled (ice bath) and acidified with 1 equivalent of concentrated HCl (4.2 ml). The resulting white precipitate was filtered and the solid washed with cold H$_2$O. After air drying overnight, 6.7 g of white crystals (84%) was obtained shown to be homogeneous by hplc analysis (Waters Ass. Micro-Bondapack C$_{18}$ column using acetonitrile/water 6:4 as eluant at a flow rate of 0.8 ml/min and refractive index detection); m.p. 157°-160° C.; IR (KBr) cm$^{-1}$: 3249 (s, H-N), 1719 (s, CO$_2$H), 1660 (s, C=O); $^1$H-NMR (DMSO-d$_6$): 6.29 and 6.10 (s, 2, H-N), 3.53 (m, 2), 2.18 (t, 2), 1.38 (m, 8), 1.02 (d, 3); $^{13}$C-NMR (DMSO-d$_6$): 174.7 (s), 163.1 (s), 55.1 (d), 50.3 (d), 33.6 (t), 29.5 (t), 28.6 (t), 25.6 (t), 24.4 (t), 15.5 (q); mass spectrum e/V (70 eV) 214 (parent), 155 (p-CH$_2$CO$_2$H), 99 (base).

Analysis Calculated for C$_{10}$H$_{18}$N$_2$O$_3$: C, 56.05; H, 8.46; N, 13.07%. Found: C, 55.86; H, 8.22; N, 12.97%.

EXAMPLE 13

1,3-Diacetyl-4-methyl-5-(5-ethoxycarbonyl-pentanoyl)-4-imidazolin-4-one

4-Methyl-5-(5-ethoxycarbonylpentanoyl)-4-imidazolin-2-one (5.0 g, 19.7 mmol) in 25 ml of acetic anhydride was refluxed for 3 hours, the acetic anhydride removed in vacuo and an additional 25 ml of acetic anhydride added. After refluxing an additional 3 hours, the solvent was again removed in vacuo, the residue taken up in ether from which crystallized a white material, 7.2 g, (100%), which was homogeneous by tlc analysis (silica gel, CHCl$_3$/HOAc 28:2, visualization by phosphomolybdic acid). The crude product was recrystallized from ethanol/water 2:1 to afford 4.75 g (71%) of material for analysis; m.p. 71°-71.5° C.; IR (film) cm$^{-1}$: 1728 (s), 1696 (s), 1620 (w); $^1$H-NMR (CDCL$_3$, 250 MHz): 4.16 (t, 2, J=7.0 Hz), 2.68 (s, 3), 2.65 (s, 3), 2.41 (t, 2), 2.34 (s, 3), 2.32 (t, 2), 1.67 (m, 4), 1.26 (t, 3, J=7.0 Hz); $^{13}$C-NMR (CDCl$_3$): 193.8, 173.3, 170.0, 168.5, 149.8, 125.7, 120.8, 60.2, 42.4, 33.8, 26.2, 24.5, 24.2, 23.7, 14.1, 12.0.

Analysis Calculated for C$_{16}$H$_{22}$N$_2$O$_6$: C, 56.80; H, 6.55; N, 8.28%. Found: C, 56.66; H, 6.53; N, 8.21%.

EXAMPLE 14

1,3-Diacetyl-4-bromomethyl-5-(5.-ethoxycarbonylpentanoyl)-4-imidazolin-2-one A slurry of 10.8 g (31.9 mmol) of product of the preceding Example, 5.84 g (32 mmol) of N-bromosuccinimide and 10 mg of benzoylperoxide in 200 ml of CCl$_4$ was refluxed for 3 hours, whereupon tlc analysis indicated the complete consumption of starting material (silica gel, ethyl acetate/hexane 1:1, visualization by phosphomolybdic acid). The reaction was cooled, the succinimide removed by filtration and the filtrate concentrated in vacuo to an oil which when triturated with ether crystallized affording after filtration, 10.97 g (83%) of title product; m.p. 114°-115° C.; IR (film) cm$^{-1}$ 1745 (s), 1722 (s), 1690 (m); $^1$H-NMR (CDCl$_{13}$): 4.64 (s, 2), 4.05 (q, 2), 2.64 (s, 3), 2.58 (s, 3), 2.40 (m, 4), 1.61 (m, 4), 1.21 (t, 3); $^{13}$C-NMR (CDCl$_3$): 193.6, 173.5, 169.6, 168.6, 149.3, 124.5, 123.5, 60.4, 42.4, 34.0, 29.6, 26.2, 24.6, 24.3, 23.8, 20.5, 14.3.

EXAMPLE 15

1,3-Diacetyl-4-(4-ethoxycarbonylbutanoyl)-1H,3H-thieno[3,4-d]l imidazol-2-one

[dl-1,3-Diacetyl-3a,6a-di(dehydro)biotin Ethyl Ester]

A solution of 7.43 g (29 mmol) Na$_2$S$_2$O$_3$.5H$_2$O in 150 ml water was added to a solution of 12.5 g (29 mmol) 1,3-diacetyl-4-bromomethyl-5-(5-ethoxycarbonylpentanoyl)-4-imidazolin-2-one in 150 ml acetonitrile. After stirring for 30 minutes at room temperature, the solvents were evaporated in vacuo to give the corresponding Bunte salt (—Br→—S—SO$_3$Na) as a white solid (contaminated with an equivalent amount of sodium bromide) This solid was dissolved in 125 ml glacial acetic acid and 5.71 g (30 mmol) p-toluenesulfonic acid monohydrate were added. After stirring at room temperature for 1.5 hours, 125 ml methylene chloride and 100 ml water were added and the layers were separated.

To the organic layer was slowly added saturated NaHCO$_3$ to adjust the pH of the mixture to 8.0. The aqueous layer was separated and extracted with 100 ml fresh methylene chloride. The combined organic layers were washed with brine, dried (MgSO$_4$), and the solvent evaporated to give 10.0 g (96.5%) of the title compound as an oil, which crystallized on standing; $^1$H-NMR 1.22 (t, 3, OCH$_2$CH$_3$), 1.45–1.8 (m, 4, 2CH$_2$), 2.28 (t, 2, CH$_2$COOEt), 2.48 and 2.50 (2s, 6, N—COCH$_3$'s), 3.03 (t, 2, CH$_2$), 4.07 (q, 2, OCH$_2$CH$_3$), and 7.13 ppm (s, 1, aromatic proton)

The intermediate Bunte salt, containing NaBr, was alternatively prepared employing 120 ml of tetrahydrofuran in place of the acetonitrile and reaction time of 45 minutes prior to evaporation of solvent. In either case, the Bunte salt shows $^1$H-NMR (CDCl$_3$): 1.16 (t, 3, CO$_2$CH$_2$CH$_3$, 1.38–1.95 (m, 4, 2CH$_2$'s), 2.03–2.47 (m, 4, 2CH$_2$'s), 2.58 (s, 3, NCOCH$_3$), 2.62 (s, 3, NCOCH$_3$), 4.03 (q, 2, CO$_2$CH$_2$CH$_3$) and 4.35 ppm (broad s, 2, CH$_2$SSO$_3$Na); and tlc Rf 0.58 (4:1 ethyl acetate:methanol; u.v. visualization).

EXAMPLE 16

1,3-Di(Methoxycarbonyl)-4-methyl-5-5-ethoxycarbonylpentanoyl)-4-imidazolin-2-one A mixture of 1.88 g (7.4 mmol) of 4-methyl-5-(5-ethoxycarbonylpentanoyl)-4-imidazolin-2-one and 20 ml methyl pyrocarbonate was heated to 90° C. and stirred for 1.5 hours whereupon a complete solution was obtained. After removal of the volatiles in vacuo, the oily residue was treated with 20 ml hexanes to give a white solid which was collected by filtration and washed with two 5 ml portions of hexanes. Recrystallization from 100 ml ethyl ether gave 2.1 g (76.6%) of the title compound; m.p. 74°–76° C.; $^1$H-NMR (CDCl$_3$): 1.27 (t, 3, OCH$_2$CH$_3$); 1.58–1.76 (m, 4, 2CH$_2$'s), 2.33 (t, 2, CH$_2$), 2.38 (s, 3, CH$_3$), 2.57 (t, 2, CH$_2$), 3.98 (s, 3, NCOOCH$_3$), 4.01 (s, 3, NCOOCH$_3$) and 4.14 ppm (q, 2, OCH$_2$CH$_3$); $^{13}$C-NMR δ (CDCl$_3$) 11.9, 14.2, 23.1, 24.3, 34.0, 41.8, 54.8, 55.1, 60.3, 120.9, 126.5, 146.4, 149.9, 150.2, 173.2, and 192.6 ppm.

Analysis Calculated for C$_{16}$H$_{22}$O$_8$N$_2$: C, 51.88; H, 5.99; N, 7.57%. Found: C, 51.77; H, 6.30; N, 7.81%.

EXAMPLE 17

1,3-Di(methoxycarbonyl)-4-(bromomethyl)-5-(5-ethoxycarbonylpentanoyl)-4-imidazolin-2-one To a solution of 1.6 g (4.3 mmol) of the product of the preceding Example in 35 ml carbon tetrachloride was added 0.765 g (4.3 mmol) N-bromosuccinimide and 90 mg benzoyl peroxide, and the mixture was heated to reflux for 1 hour. After filtration, the solvent was removed in vacuo to give 2.01 g of the title compound as a yellow oil; $^1$H-NMR (CDCl$_3$): 1.22 (t, 3, OCH$_2$CH$_3$), 1.45–1.85 (m, 4, 2CH$_2$'s), 2.28 (t, 2, CH$_2$), 2.56 (t, 2, CH$_2$), 3.98 and 4.02 (2s's, 6, NCOOCH$_3$), 4.02 (q, 2, OCH$_2$CH$_3$), and 4.61 ppm (s, 2, CH$_2$Br).

EXAMPLE 18

1,3-Di(methoxycarbonyl)-4-(4-ethoxycarbonylbutanoyl)-1H,3H-thieno[3,4-d]imidazol-2-one

[dl-1,3-Di(methoxycarbonyl)-3a,6a-di(dehydro)biotin Ethyl Ester]

A solution of 1.03 g (4.1 mmol) NaS$_2$O$_3$.5H$_2$O in 40 ml water was added to a solution of 2.0 g (4.1 mmol) product of the preceding Example in 40 ml acetonitrile. The mixture was stirred at ambient temperature for 1.5 hours and then the solvent was evaporated in vacuo. The residue was mixed with 20 ml toluene and reevaporated. Toluene treatment was repeated once to finally give 2.5 g of the corresponding Bunte salt as a yellow solid (contaminated with an equivalent amount of sodium bromide); $^1$H-NMR (CD$_3$OD): 1.22 (t, 3, CO$_2$CH$_2$CH$_3$), 1.43–1.83 (m, 4, 2CH$_2$'s), 2.27 (t, 2, CH$_2$), 2.67 (t, 2, CH$_2$), 3.91 (s, 3, NCO$_2$CH$_3$), 3.97 (s, 3, NCO$_2$CH$_3$), 4.07 (q, 2, CO$_2$CH$_2$CH$_3$) and 4.32 (s, 2, CH$_2$SSO$_3$Na); tlc Rf 0.38 (4:1 ethyl acetate:methanol; u.v. visualization). This salt was taken up with 25 ml glacial acetic acid and to the mixture was added 0.779 g (4.1 mmol) p-toluenesulfonic acid monohydrate. After stirring at ambient temperature for 1 hour, 25 ml water and 25 ml methylene chloride were added to the mixture and stirring was continued for 10 minutes. The layers were then separated, the aqueous layer was reextracted with 25 ml methylene chloride, and to the combined organic extracts was added 20 ml saturated NaHCO$_3$. Finally, to the mixture was added, dropwise, 40% sodium hydroxide solution to adjust the pH to 9.0. After separation of the layers, the aqueous layer was reextracted with 20 ml methylene chloride, the combined organic layers were washed with 20 ml brine, dried (MgSO$_4$), and the solvent was evaporated in vacuo to give 1.3 g (82.8%) of the title compound as a light yellow oil which solidified on standing; $^1$H-NMR (CDCl$_3$): 1.23 (t, 3, OCH$_2$CH$_3$), 1.48–1.9 (m, 4, 2CH$_2$'s), 2.3 (t, 2, CH$_2$), 3.0 (t, 2, CH$_2$), 4.05 (2s, 6, 2 NCOOCH$_3$'s), 4.07 (q, 2, OCH$_2$CH$_3$), and 6.87 ppm (s, 1, aromatic proton); tlc Rf 0 70 (ethyl acetate:methanol 4:1, u.v. visualization). After recrystallization from ether for analysis: m.p. 90.5°–91.5° C.

Analysis Calculated for C$_{16}$H$_{20}$O$_7$N$_2$S: C, 49.99; H, 5.24; N, 7.29%. Found: C, 49.85; H, 5.23; N, 7.22%.

EXAMPLE 19

1,3-Diacetyl-4-methyl-5-hexanoyl-4-imidazolin-2-one

A solution of 8.0 g (40.8 mmol) of 4-methyl-5-hexanoyl-4-imidazolin-2-one in 40 ml of acetic anhydride was refluxed under N$_2$ for 2 hours, the solvent removed in vacuo and replaced with an additional 40 ml fresh acetic anhydride. After an additional 3 hours at reflux, the reaction was cooled, solvent removed in vacuo and the resulting oil taken up in 100 ml of ethanol. Crystallization by reevaporation in vacuo gave 9.18 g (80%) of white crystals; m.p. 71°–72° C.; IR (film) cm$^{-1}$: 1745 (s), 1729 (s), 1690 (m), 1620 (w); $^1$H-NMR (CDCl$_3$): 2.60 (s, 3), 2.61 (s, 3), 2.41 (m, 2), 2.26 (s, 3), 1.34 (m, 6), 0.84 (t, 3).

Analysis Calculated for C$_{14}$H$_{20}$N$_2$O$_4$: C, 59.98; H, 7.19; N, 9.99%. Found: C, 59.85; H, 6.90; N, 9.92%.

EXAMPLE 20

1,3-Diacetyl-4-(bromomethyl)-5-hexanoyl-4-imidazolin-2-one

A solution of 8.0 g (28.6 mmol) of title product of the preceding Example,, 5.19 g (28.0 mmol) of N-bromosuccinimide and 10 mg of benzoylperoxide in 100 ml of CCl$_4$ was refluxed for 3 hours whereupon tlc analysis showed the complete consumption of starting ketone. The reaction was cooled, CCl$_4$ removed in vacuo and the residue taken up in ethanol. Slow cooling afforded after isolation by filtration and drying, 6.97 g (67%) of white crystals. Concentration in vacuo afforded an additional 3.34 g of white crystals for a total crude yield of 10.21 g (100%). Both crops were homogeneous by tlc analysis; IR (CDCl$_3$) cm$^{-1}$: 1745 (s), 1730 (s), 1682 (s), 1618 (m); $^1$H-NMR 4.64 (s, 2), 2.69 (s, 3), 2.65 (s, 3), 2.47 (m, 2), 1.63 (m, 2), 1.30 (m, 4), 0.89 (t, 3); mass spectrum (70 eV) m/e 316, 318 (parent Ac), 274, 276 (parent-2Ac), 237 (parent-Br and Ac), 195 (parent-Br and 2Ac), 43 (base, Ac).

Analysis Calculated for C$_{14}$H$_{19}$N$_2$O$_4$Br: C, 46.81; H, 5.33; N, 7.80%. Found: C, 46.59; H, 5.18; N, 7.69%.

EXAMPLE 21

1,3-Diacetyl-4-pentyl-1H,3H-thieno[3,4d]imidazol-2-one

A solution of 172 mg (0.69 mmol) Na$_2$S$_2$O$_3$.5H$_2$O in 3 ml water was added to a solution of 247 mg (0.69 mmol) product of the preceding Example in 3 ml acetonitrile. After stirring for 21 hours at room temperature, the solvents were removed in vacuo leaving the corresponding Bunte salt (—Br—→—S—SO$_3$Na) as a white solid contaminated with an equimolar amount of sodium bromide; $^1$H-NMR δCD$_3$OD: 0.7–1.83 (m, 9, sidechain), 2.43–2.7 (m, 2, COCH$_2$), 2.57 (s, 3, NCOCH$_3$), 2.63 (s, 3, NCOCH$_3$) and 4.3 ppm (s, 2, CH$_2$SSO$_3$Na); tlc Rf 0.56 (silica gel, 4:1 ethyl acetate:methanol, u.v. visualization)]. This solid was taken up in 5 ml glacial acetic acid and to the mixture was added 131 mg (0.69 mmol) p-toluenesulfonic acid monohydrate. After stirring at room temperature for four hours, most of the solvent was evaporated in vacuo, and 10 ml methylene chloride and 5 ml water were added. The organic layer was then washed with 15 ml saturated NaHCO$_3$ and then brine, dried (MgSO$_4$), and the solvent was removed in vacuo to give 177 mg (87.2%) of the title compound as a gummy solid. $^1$H-NMR (Me$_4$Si) δCDCl$_3$: 0.88 (t, 3, CH$_2$CH$_3$), 1.1–1.8 (m, 6, 3CH$_2$), 2.50 and 2.53 (2s, 6, 2N-Acs), 3.03 (t, 2, CH$_2$) and 7.13 ppm (s, 1, aromatic proton).

EXAMPLE 22

1,3-Di(methoxycarbonyl)-4-methyl-5-hexanoyl-4-imiidazolin-2-one

A mixture of 1.9 g (9.68 mmol) 4-methyl-5-hexanoyl-4-imidazolin-2-one and 20 ml dimethyl pyrocarbonate was stirred and heated to 95° C. for 1.5 hours. The resulting solution was cooled to room temperature and evaporated in vacuo to a white solid, which was recrystallized from ether to give 2.41 g (79.8%) of title compound; m.p. 84°–86° C.; $^1$H-NMR (CDCl$_3$): 0.87 [t, 3, CH$_2$CH$_3$), 1.03–1.90 (m, 6, 3CH$_2$'s), 2.33 (s, 3, CH$_3$), 2.41 (2, t, COCH$_2$), 3.90 (s, 3, NCOOCH$_3$) and 3.93 ppm (s, 3, NCOOCH$_3$).

EXAMPLE 23

1,3-Di(methoxycarbonyl)-4-bromomethyl-5-hexanoyl-4-imidazolin-2-one

To a solution of 2.03 g (6.5 mmol) product of the preceding Example in 35 ml carbon tetrachloride was added 1.16 g (6.5 mmol) N-bromosuccinimide and 21 mg benzoyl peroxide, and the mixture was refluxed for 30 minutes. After cooling to room temperature and filtering, the solvent was evaporated in vacuo to give 2.54 g of an oil which solidified on standing. This solid was recrystallized from 35 ml ether to give 1.68 g (66.1%) of the title compound; m.p. 71°–73° C.; $^1$H-NMR δ(CDCl$_3$): 0.85 (t, 3, CH$_3$), 1.2–1.32 (4, m, 2CH2's), 1.55–1.68 (2, m, CH$_2$), 2.51 (2, t, COCH$_2$), 3.95 (3, s, NCOOCH$_3$), 3.99 (3, s, NCOOCH$_3$) and 4.61 ppm (3, s, CH$_2$Br); $^{13}$C-NMR 67 (CDCl$_3$). 193.2, 149.5, 149.2, 145.4, 124.2, 122.9, 55.2, 55.0, 42.1, 31.1, 24.1, 22.2, 19.7, 13.7.

Analysis Calculated for C$_{14}$H$_{19}$N$_2$O$_6$Br: C, 42.98; H, 4.89; N, 7.16%. Found: C, 42.60; H, 4.80; N, 7.01%

EXAMPLE 24

1,3-Di(methoxycarbonyl)-4-pentyl-1H,3H-thieno[3,4-d]imidazol-2-one

A solution of 0.98 g (3.94 mmol) Na$_2$S$_2$O$_3$.5H$_2$O in 40 ml water was added to a solution of 1.54 g (3.94 mmol) product of the preceding Example, and the mixture was stirred at ambient temperature for 1 hour. The solvents were then removed in vacuo and the residue was dried, by charging and removing in vacuo three 20 ml portions of toluene, to give the corresponding Bunte salt as a white solid (contaminated with an equimolar amount of sodium bromide). This salt was dissolved in 25 ml glacial acetic acid, 750 mg (3.95 mmol) p-toluenesulfonic acid monohydrate was added, and the mixture was stirred at room temperature for 2 hours, at which time 25 ml water and 25 ml methylene chloride were added to the mixture and stirring was continued for 10 minutes. The layers were then separated, the aqueous layer was reextracted with 25 ml methylene chloride, and to the combined organic extracts was added 20 ml saturated solution of sodium bicarbonate. Finally, to the mixture was added, dropwise, 40% sodium hydroxide solution to adjust the pH at 9.0. After separation of the layers, the aqueous layer was reextracted with 20 ml methylene chloride, the combined organic layers were washed with 20 ml brine, dried (MgSO$_4$), and the solvent was evaporated in vacuo to give 1.23 g (96.1%) of the title compound; $^1$H-NMR (CDCl$_3$): 0.87 (t, 3, CH$_2$CH$_3$), 1.05–1.9 (m, 6, 3CH$_2$'s), 2.95 (t, 2, CH$_2$), 3.98 (s, 6, 2NCOOCH$_3$'s) and 6.8 ppm (s, 1, aromatic proton). For elemental analysis, a small sample was recrystallized from ether/hexane; m.p. 99°–102° C.

Analysis Calculated for C$_{14}$H$_{18}$O$_5$N$_2$S: C, 51.52; H, 5.56; N, 8.59%. Found: C, 51.10; H, 5.58; N, 8.47%.

EXAMPLE 25 dl-Biotin 1,3-Di(methoxycarbonyl)-4-(4-ethoxycarbonylbutyl)-1H,3H-thieno(3,4-d)imidazol-2-one (1.45 g) in 100 ml of acetic acid was hydrogenated at 100° C. and 70 atmospheres over 2.4 g 10% Pd/C for 16 hours. The catalyst was recovered by filtration and the filtrate evaporated in vacuo to yield 1.3 g of brown oil. The latter was combined with 100 ml H$_2$O and 3.17 g Ba(OH)$_2$.8H$_2$O and the mixture refluxed for 3.5 hours, at which time the mixture was cooled, ad3usted to pH 2.5 by the dropwise addition of 1N HCl, and filtered. The filtrate was evaporated to 50 ml and then cooled slowly to 0° C. The resulting title product was recovered by filtration, using 5 ml of 1N HCl for wash, to yield 0.49 g (54.3%), m.p. 218°–222° C., identical in properties with known dl-biotin.

EXAMPLE 26 dl-Descarboxybiotin (4-Pentylperhydrothieno(3,2-b)imidazol-2-one)

1,3-Di(methoxycarbonyl)-4-pentyl-1H,3H-thieno[3,4-d]-imidazol-2-one (1.4 g) in 100 ml of acetic acid was hydrogenated at 70° C. and 70 atmospheres over 4.2 g of 10% Pd/C for 3 hours. Catalyst was recovered by filtration and the filtrate evaporated in vacuo to yield 1.4 g of a gummy oil. The latter was dissolved in 35 ml of methanol and 9.4 ml of 1N NaOH added. The mixture was stirred 2 hours, partially evaporated (removing most of the methanol), and title product recovered by filtration, 0.705 g (69.1%), m.p. 140°–144° C., identical in properties with the known product.

I claim:

1. A compound of the formula

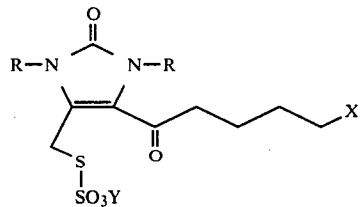

wherein R is $(C_1-C_5)$alkanoyl or $(C_2-C_5)$alkoxycarbonyl, X is methyl or $(C_2-C_5)$alkoycarbonyl and Y is an alkali metal, with the proviso that when R is acetyl, X is other than ethoxycarbonyl.

2. A compound of claim 1 wherein R is acetyl, propionyl or methoxycarbonyl and X is methyl, methoxycarbonyl or ethoxycarbonyl.

3. The compound of claim 2 wherein R is acetyl, X is methyl and Y is sodium.

4. The compound of claim 2 wherein R is methoxycarbonyl, X is methyl and Y is sodium.

5. The compound of claim 2 wherein R is methoxycarbonyl, X is ethoxycarbonyl and Y is sodium.